United States Patent
Korpela et al.

(10) Patent No.: US 9,733,300 B2
(45) Date of Patent: Aug. 15, 2017

(54) CORROSION DETECTION SYSTEM

(71) Applicant: KONE Corporation, Helsinki (FI)

(72) Inventors: Jukka Korpela, Hyvinkää (FI); Mikko Vaskela, Rajamäki (FI)

(73) Assignee: Kone Corporation, Helsinki (FI)

( * ) Notice: Subject to any disclaimer, the term of this patent is extended or adjusted under 35 U.S.C. 154(b) by 86 days.

(21) Appl. No.: 14/610,801

(22) Filed: Jan. 30, 2015

(65) Prior Publication Data
US 2015/0145552 A1 May 28, 2015

Related U.S. Application Data

(63) Continuation of application No. PCT/EP2012/066386, filed on Aug. 23, 2012.

(51) Int. Cl.
*G01R 31/00* (2006.01)
*G01R 31/28* (2006.01)
*G01N 17/00* (2006.01)

(52) U.S. Cl.
CPC ......... *G01R 31/2813* (2013.01); *G01N 17/00* (2013.01); *G01R 31/2812* (2013.01); *G01R 31/2818* (2013.01)

(58) Field of Classification Search
CPC ............... H01L 24/81; H01L 24/83; H01L 2224/73265; G01N 17/00; G01N 17/04; G01N 27/223; G01N 17/006; G01N 21/31; G01N 27/045; H05K 3/002; H05K 3/3463; H05K 1/0266; H05K 2201/0358; H05K 2201/0761; H05K 3/326; H05K 3/341; H05K 3/4688; G01R 31/2801; G01R 31/025; G01R 19/25; G01R 27/06; G01R 31/281; G01R 31/2812; G01R 31/2818; G01R 31/2813; H01R 12/515; H01R 12/58; H01R 4/184; H01R 4/26; H01R 4/5008; H01R 12/87; H01R 23/70; H01R 12/88; G06F 3/041
See application file for complete search history.

(56) References Cited

U.S. PATENT DOCUMENTS

| | | | |
|---|---|---|---|
| 2005/0269213 A1* | 12/2005 | Steimle | G01N 17/04 205/775.5 |
| 2012/0032700 A1 | 2/2012 | Sugane | |
| 2014/0152449 A1* | 6/2014 | Klein | H05K 1/0268 340/662 |

FOREIGN PATENT DOCUMENTS

| | | |
|---|---|---|
| CN | 2466634 Y | 12/2001 |
| DE | 4105440 A1 | 8/1992 |
| JP | 3-33665 A | 2/1991 |
| JP | 410073629 A * | 3/1998 |
| JP | 10-239374 A | 9/1998 |
| JP | 2000-304801 A | 11/2000 |

(Continued)

*Primary Examiner* — Vinh Nguyen
(74) *Attorney, Agent, or Firm* — Birch, Stewart, Kolasch & Birch, LLP

(57) ABSTRACT

A printed circuit arrangement employs a printed circuit board having a corrosion test circuit provided with at least two conductive pads which are located proximate to each other in a measuring area. The arrangement uses a measuring device to identify corrosion on other defects in the circuit board including short circuits and/or line cuts. One pad is an excitation pad, being connected to an excitation signal source, and the other pad is a response pad, whereby the measuring device is connected at least to the response pad.

13 Claims, 3 Drawing Sheets

(56) References Cited

FOREIGN PATENT DOCUMENTS

| | | |
|---|---|---|
| JP | 2001-251026 A | 9/2001 |
| JP | 2003-4801 A | 1/2003 |
| WO | WO 94/01757 A1 | 1/1994 |

* cited by examiner

CORROSION DETECTION SYSTEM

CROSS REFERENCE TO RELATED APPLICATIONS

This application is a Continuation of PCT International Application No. PCT/EP2012/066386 filed on Aug. 23, 2013, which is hereby expressly incorporated by reference into the present application.

The present invention relates to a printed circuit arrangement which is provided on printed circuit board (PCB) and comprises a corrosion test circuit. Such kind of printed circuit arrangement is known from JP200304801A. This arrangement comprises two conductive pads located on a printed circuit board which pads are arranged in a measuring area in a given mutual distance to each other. Both pads are connected to the power source and a measuring device is provided in the supply line of one of the two pads. With this arrangement it is possible to measure an insulation resistance failure of the PCB. Accordingly, although it is possible to measure short circuits within the printed circuit board it is not possible to identify a PCB line cut which may also occur when the PCB is exposed to corrosion.

It is therefore object of the invention to provide a printed circuit arrangement which is able to identify insulation resistance failures of the printed circuit board as well as a line cuts occurring due to corrosion of the printed circuit board.

The above mentioned object is solved with the present invention via the features of claim 1. Preferred embodiments of the invention are subject matter of the dependent claims.

The printed circuit arrangement of the invention comprises a printed circuit board having a corrosion test circuit comprising at least two conductive pads which are a in measuring area located proximate to each other. The arrangement further comprises a measuring device, which is able to measure the voltage of at least one pad or the capacitance between both pads. According to the invention one pad works as an excitation pad, being connected to an excitation signal source. The other pad works as a response pad, whereby the measuring device is connected at least to the response pad.

The printed circuit arrangement allows different kinds of corrosion measurements of the printed circuit board. In any case the basic principle of the invention is the excitation of the excitation pad, e.g. via a potential difference or via a pulse signal and the measurement of the voltage of the response pad or the interaction between both pads.

Via the invention it is possible to easily monitor and identify the progress of corrosion of a printed circuit board which in an elevator shaft often undergoes a higher corrosion because of the environmental conditions.

In a first measuring method the first end of the excitation pad is connected to a first potential, e.g. ground, and the second end is connected to a second, different potential, (e.g. supply voltage: VCC) via a first resistor. Now, as the response pad is connected to VCC via a second resistor, a short circuit between the excitation pad and the response pad causes in the response pad voltage drops from said second potential (e.g. VCC) to the first potential (e.g. ground: GND), which voltage drop can be detected at the input IN2 of the measuring device.

On the other hand, if corrosion causes a cut of the excitation pad, the corrosion detection arrangement cannot work any longer. Therefore, a cut of the excitation pad causes a voltage rise in the measurement input IN1 of the excitation pad into the measuring device from GND to VCC which is interpreted by the measuring device as a cut of the corrosion detection arrangement, which thus can easily be detected.

A problem may arise with above-disclosed embodiment in that if a cut happens in the response pad the measurement arrangement does not work any longer. Therefore, it would be beneficial to detect this too. On this behalf, in a preferred embodiment a terminal resistor $R_A$ is connected between the end of response pad and ground. Because of said terminal resistor $R_A$, the voltage in measurement input IN2 of the response pad into the measuring device is normally at a defined level between the two different potentials, preferably between GND and VCC. If now a corrosion based cut occurs in the response pad the voltage in the measurement input IN2 will rise to VCC. Therefore, also a cut in the response pad can be detected. This further embodiment however requires that the input IN2 of the response pad must be an analog input which can detect voltages between the two different potentials, e.g. between VCC and GND, accurately.

It must be noted that above-disclosed further embodiment with the additional terminal resistor $R_A$ is not necessary, but it provides the possibility that also a cut in the response pad can be detected.

In a preferred embodiment of the invention a potential difference is applied to opposite ends of the excitation pad.

The inventive printed circuit arrangement allows a second measuring method wherein a pulse signal is input to the excitation pad and the capacitance between both pads can be measured from the current flowing through the resistor connected between the response pad and GND in response to the pulse signals fed to the excitation pad, resulting in a voltage response signal at the connection of the response pad to the measuring device. In this arrangement the excitation pad is connected to a pulse signal source and the response pad is connected to the measuring device. In this connection it is to be noted that the measuring device is preferably a microprocessor which is able to output excitation pulses as well as to perform voltage or capacitance measurements.

The progress of corrosion can be detected by a change of the capacitance between both pads and a corresponding change of the voltage measured at the connection terminal of the response pad to the measuring device.

If the measuring device is or comprises a microprocessor the measuring device may be configured to send a signal to the elevator or to any maintenance location of the elevator when the corrosion has reached a certain value indicating that the PCB in question should be changed in connection with the next maintenance visit. It could also be used as a signal that other printed circuit arrangements in the elevator are to be replaced.

Preferably, in this case the response pad is connected at a connection point via a terminal resistor to a defined first potential, e.g. ground. Via this simple circuit, the capacitive interaction between the excitation pad and the response pad leads to a current flow through a terminal resistor connected between the response pad and GND, which can be easily be measured as a voltage response signal at the input of the response pad into the measuring device.

Of course, the pulse signal could be fed to the excitation pad via an external pulse generator. In a compact arrangement having sparse components the measuring device comprises a microprocessor configured to output a pulse signal to the excitation pad. In this case the measuring device also outputs the excitation signals to the excitation pad.

Preferably both pads are connected via first and second resistors to a defined second potential, preferably VCC, to keep the pads on a defined absolute and mutual potential level.

Preferably, the measuring device comprises a microprocessor configured to measure the voltage in both pads and/or the capacity between them. This allows the performance off different tests on the printed circuit without modifications of the lay-out.

Preferably, the pads are located on one side of the board so that the condition of the printed connective pads as well as a condition of the printed circuit board between these pads can be visually monitored. Also, this kind of one-layer PCB circuit is also cheaper to manufacture.

Although usually the terminal resistor is arranged on the same side of PCB as the pads it may be connected to the end of the first pad via a connective through hole through the board. This arrangement makes it easy to locate the terminal resistor without disturbing the arrangement of the pads in the measuring area. On the other hand in the area of a through hole the corrosion of a PCB is higher than on the surface so that the provision of a through hole enhances the corrosion information of the PCB.

Preferably, through holes are adapted to excitation pad and/or response pad because they speed up progress of corrosion, therefore progress of corrosion can be detected and information of this can be sent to maintenance center before the functional circuit of PCB board is damaged.

Preferably, the two pads are located parallel to each other at least in the measuring area. Via this arrangement defines capacity can easily be set via a corresponding distance between the two pads. The distance is preferably smaller than the width of the pad. To speak in absolute values the mutual distance of both pads in the measuring area should be below 0.3 mm, at least below 0.5 mm.

Preferably, the two pads have a meandering layout in the measuring area which leads to an increased length of the parallel pads in the measuring area and therefore facilitates capacitance measurements and covers an essential part of the printed circuit board in the measuring area.

Preferably, the measuring device comprises a microprocessor which is able to input pulses to either of both pads. On the other hand both connectors of the measuring of the microprocessor to the pads may be used as an input line so that any kind of current voltage inductance or capacity measurements can be performed via the microprocessor.

The measuring device, particularly the microprocessor may be located fixedly on the board to achieve a compact structure of the whole arrangement.

On the other hand it is possible to provide the measuring device particularly the microprocessor as a separate device, e.g. as a handheld device or at a device at a remote center of the elevator company. This separate measuring device may be connected to the printed circuit board at the second ends of the pads which preferably form contactors for the measuring device. In this case it is not necessary to provide the measuring device for each elevator. Rather each elevator may be provided with a printed circuit arrangement without the measuring device and the measuring device may be a hand held device which is successively connected to all the printed circuit arrangement which are fixed on a printed circuit board in the elevator shaft to get information about the actual corrosion status of the corresponding printed circuit board. It is also possible to measure the corrosion of the printed circuit at the elevator company, e.g. when the printed circuit has been replaced during repair or maintenance. Thereby it is possible to get afterwards information about the corrosion status of the printed circuit.

The printed circuit arrangement may be a separate arrangement besides printed circuit arrangements used in the elevator shaft as for example the elevator control. It is of course also possible to provide the pads and other components of the printed circuit arrangement on printed circuit as part of an elevator control or as part of any other electronic device used in the elevator.

The conductive pads need not to be located only on one side of the printed circuit boards but may provide one or several through holes so that parts of the pads can be provided on both opposite sides of the printed circuit board. As through holes provide an area of increased corrosion with a printed circuit board a corresponding pad layout may be as enhanced and better information about the corrosion of a printed circuit board.

Preferably, the PCB pad pattern according to the invention is situated under some PCB board connector, because that area is typically exposed to corrosion.

By means of invention embodiment 1, it is possible to monitor operation condition of monitoring arrangement by monitoring cut of excitation pad (and/or cut of response pad, see my further embodiment with $R_A$)

The invention is now described with the aid of the schematic drawing.

Figure 1:
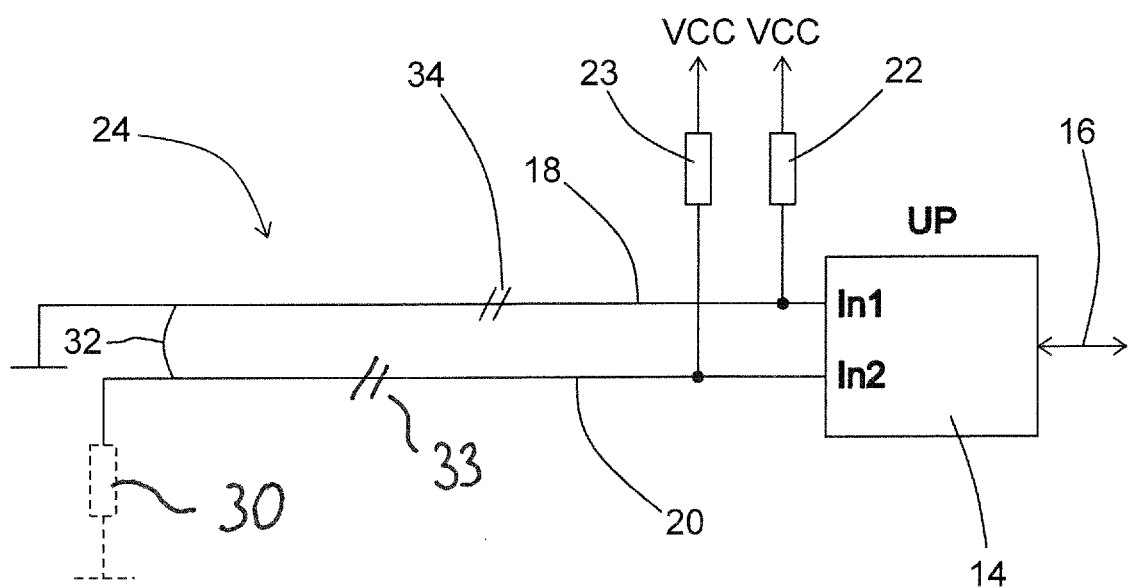
FIG. 1 shows a diagram of a printed circuit arrangement.

FIG. 1 shows a printed circuit arrangement 10 including a printed circuit board 12 carrying a measuring device 14 which preferably is or comprises a microprocessor. The measuring device 14 has a data connection 16 to an elevator control, a remote maintenance center, a memory or any other devices which are able to store or to process corrosion measurement data. The measuring device has a first input terminal In1 which is connected with a first conducting pad 18 which functions as an excitation pad. A second terminal In2 of the measuring device is connected to a second conductive pad 20 functioning as response pad. Both pads 18, 20 are connected via first and second resistors 22, 23 to the supply voltage VCC. The pads 18, 20 run parallel to each other and preferably in a distance of less than 0.3 mm. In a measuring area 24 the pads 18, 20 are preferably arranged in a meandering layout (not shown). Whereas the second ends of both pads 18, 20 are connected with the input terminals In1, In2 of the measuring device 14 the second end of the excitation pad 18 is connected to ground. The first end of the response pad 20 is either free or connected via a terminal resistor 30 to ground.

The arrangement works as follows:

As the response pad 20 is connected to VCC via the second resistor 23, a short circuit between the excitation pad 18 and the response pad 20 causes in the response pad 20 a voltage drop from VCC to GND, which voltage drop can be detected at the input IN2 of the measuring device 14.

On the other hand, if corrosion causes a cut 34 of the excitation pad 18, the corrosion detection arrangement cannot work any longer. Therefore, a cut of the excitation pad causes a voltage rise in the measurement input IN1 of the excitation pad 18 into the measuring device 14 from GND to VCC which is interpreted by the measuring device 14 as a cut 34, which thus can easily be detected.

FIG. 1. shows in dotted lines an optional terminal resistor 30 connected between the end of response pad 20 and GND. The arrangement with the terminal resistor 30 also allows the detection of a line cut 33 in the response pad 20. Because of said terminal resistor 30, the voltage in measurement input IN2 of the response pad into the measuring device is normally at a defined level between GND and VCC. If now a corrosion based line cut 33 occurs in the response pad 20 the voltage in the measurement input IN2 will rise to VCC. Therefore, also a cut in the response pad can be detected by this arrangement. This optional embodiment requires the input IN2 of the response pad 20 to be an analog input which can detect voltages between VCC and GND.

Figure 2:
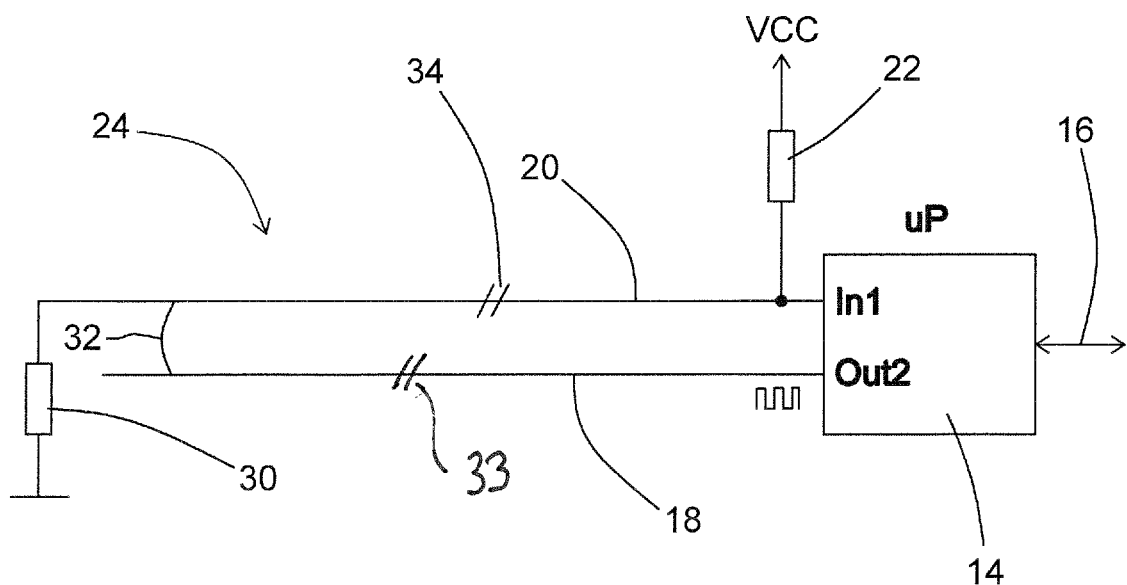
FIG. 2 shows a diagram of a second embodiment of a printed circuit arrangement for measuring the corrosion of the printed circuit board.

FIG. 2 shows a second embodiment having a measuring device 14 comprising a microprocessor connected via a first terminal Out2 to an excitation pad 18 and via a second terminal In1 to a response pad 20. The response pad 20 is connected via a first resistor 22 to VCC and via a terminal resistor 30 to GND. The measuring device has a data connection 16 to a control or a remote or maintenance facility.

The arrangement of FIG. 2 works as follows:

The measuring device 14 outputs via terminal Out2 a pulse signal to the excitation pad 18. The capacitance between both pads 18, 20 is measured from the current flowing through the terminal resistor 30 connected between the response pad 20 and GND in response to the pulse signals fed to the excitation pad. This leads to a voltage response signal at the input terminal In1 of the response pad 20 measured by the measuring device 14. In case of a short circuit the capacity between both pads drops to zero. A line cut 33 in the excitation pad 18 leads to a reduced capacity between the excitation pad 18 and the response pad 20. A line cut 34 in the response pad 20 leads to the voltage signal VCC at input terminal In1. Thus, short circuits 32 as well as line cuts 33, 34 in either pads 18,20 can be measured accurately.

Figure 3:
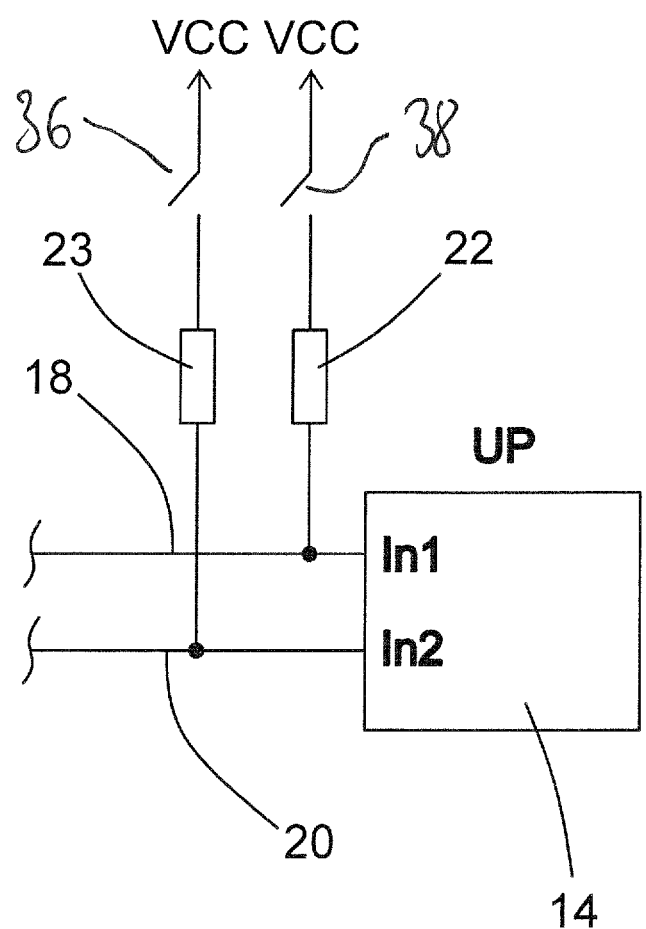
FIG. 3 shows an optional detail of the arrangement of FIG. 1.

FIG. 3 shows an optional modification of the embodiment of FIG. 1. According to FIG. 3 the connections between the pads 18, 20 and VCC via the first and second resistors 22, 23 may comprise controllable switches 36, 38. Preferably, the switches 36, 38 can be controlled via the measuring device 14. Via these switches the activity of the corrosion monitoring arrangement may arbitrarily switched on and off. By this measure the energy consumption of the circuit may be reduced, when not needed.

Of course the data connection 16 of the microprocessor 14 can be used to output measurement signals to the elevator control, to a remote maintenance center or to any data storage for later processing. Based on the measurement signals a corrosion limit signal can be issued when the corrosion as measured by the printed circuit arrangement has exceeded a certain threat hold value.

The above embodiments may be combined arbitrarily. It is also possible to provide more than two pads.

The invention claimed is:

1. Printed circuit arrangement comprising:
   a printed circuit board having a corrosion test circuit including at least two conductive pads which are in a measuring area located proximate to each other; and
   a measuring device connected to said printed circuit board so that one of said two conductive pads is an excitation pad, being connected to an excitation signal source, and the other one of said two conductive pads is a response pad, whereby the measuring device is connected at least to the response pad
   wherein the excitation pad is at its first end connected to a first potential and at its second end connected to a second potential via a first resistor;
   said measuring device thereby detecting insulation degradation or a cut in one of said conductive pads from a voltage or capacitance detected by the measuring device.

2. Printed circuit arrangement according to claim 1, wherein the response pad is connected via a terminal resistor to said first potential.

3. Printed circuit arrangement according to claim 1, wherein the measuring device comprises a microprocessor configured to output a pulse signal to the excitation pad.

4. Printed circuit arrangement according to claim 1, wherein both pads are connected via first and second resistors to said second potential.

5. Printed circuit arrangement according to claim 1, wherein the measuring device comprises a microprocessor configured to measure the voltage in both pads and/or the capacity between them.

6. Printed circuit arrangement according to claim 1, wherein the measuring device is located on the printed circuit board.

7. Printed circuit arrangement according to claim 1, wherein the measuring device is a separate device connectable to the second ends of the pads, which preferably are forming contactors for the measuring device.

8. Printed circuit arrangement according to claim 1, wherein the two pads are at least in the measuring area arranged parallel to each other.

9. Printed circuit arrangement according to claim 1, wherein the two pads are at least in the measuring area arranged in a meandering layout.

10. Printed circuit arrangement according to claim 1, wherein a given mutual distance between both pads in the measuring area is less than 0.3 mm.

11. Printed circuit arrangement according to claim 1, wherein at least one pad, preferably both pads comprises connective through holes through the board and is/are located on both sides thereof.

12. Printed circuit arrangement according to claim 1, wherein both pads are connected via the first resistor and a second resistor, the first and second resistors being of differing finite resistance to said second potential.

13. Printed circuit arrangement according to claim 1, wherein both pads are connected via the first resistor and a second resistor, the first and second resistors having differing finite resistances to said second potential.

* * * * *